(12) United States Patent
Takahashi

(10) Patent No.: US 6,365,744 B1
(45) Date of Patent: Apr. 2, 2002

(54) PROCESS FOR PRODUCING PYRIDINE DERIVATIVE THROUGH REACTION OF AZAMETALLACYCLOPENTADIENE WITH ALKYNE

(75) Inventor: Tamotsu Takahashi, Sapporo (JP)

(73) Assignee: Japan Science & Technology Corporation, Saitama-Ken (JP)

( * ) Notice: Subject to any disclaimer, the term of this patent is extended or adjusted under 35 U.S.C. 154(b) by 0 days.

(21) Appl. No.: 09/675,000
(22) PCT Filed: Jan. 11, 2000
(86) PCT No.: PCT/JP00/00075
§ 371 Date: Nov. 9, 2000
§ 102(e) Date: Nov. 9, 2000
(87) PCT Pub. No.: WO00/55135
PCT Pub. Date: Sep. 21, 2000

(30) Foreign Application Priority Data

Mar. 12, 1999 (JP) .............................. 11-65992

(51) Int. Cl.$^7$ .................. C07D 213/06; C07D 211/70
(52) U.S. Cl. ....................... 546/252; 546/348
(58) Field of Search .................. 546/252, 348

(56) References Cited

U.S. PATENT DOCUMENTS 4,477,673 A 10/1984 Kaschig
4,588,815 A 5/1986 Bonnemann

FOREIGN PATENT DOCUMENTS

EP 0110177 6/1984

OTHER PUBLICATIONS

Tamotsu Takahashi, J. Org. Chem., 1998, vol. 63, pp. 6802–6808.*
G. B. Richter–Addo, "Recent Organometallic 1,2 Nitrosyl Chemistry . . .", Chemical Review, vol. 88, No. 7, 1988, pp. 1108–1110.
Tamotsu Takahashi, et al., "Selective Intermolecular Coupling of Alkylene with Nitriles . . .", J. Org. Chem, 1998, 63, pp. 6802–6806.

* cited by examiner

Primary Examiner—D. Margaret Seaman

(57) ABSTRACT

A process for producing a pyridine derivative, which comprises reacting an azametallacyclopentadiene represented by formula (1) with an alkyne in an organic solvent containing a complex of a transition metal such as Ni(II).

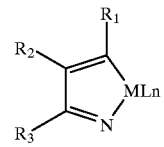

(1)

(In formula (1), M represents an early transition metal, e.g., Zr, Ti or Hf; L represents cyclopentadienyl, indenyl, fluorenyl, hydrocarbon-oxy, amide, acetylacetonato, or carboxy group, a phosphine ligand, an amine ligand, an ether ligand, or a ligand comprising two or more these bonded to each other through appropriate crosslinking group; n is an integer of 1 to 4; and $R_1$, $R_2$, $R_3$, $R_4$ and $R_5$ each represents $C_{1-20}$ (substituted) alkyl, alkenyl, an aromatic group, silyl, alkoxy, or an ester group.)

11 Claims, No Drawings

PROCESS FOR PRODUCING PYRIDINE DERIVATIVE THROUGH REACTION OF AZAMETALLACYCLOPENTADIENE WITH ALKYNE

This application is a 371 of PCT/JP00/00075, filed Jan. 11, 2000.

BACKGROUND OF THE INVENTION

1. Field of the Invention

The present invention relates to the newly developed synthetic method to produce regioselectively substituted pyridines from two different alkynes with a nitrile based on the chemical reaction between azametallacyclopendadiene, especially azametallacyclopendadiene of a pre period transition metal, and alkynes, in the presence of transition metal complex of stoichiometric amount, desirably in the presence of Ni (II) complex.

2. Description of the Prior Art

Pyridines are recognized as the very important intermediate product of various chemicals such as medicines, agricultural chemicals or bridging agents and also as the final chemical products. Therefore, it is desired for a long time to develop a method for preparation of pyridines, in which chemical reactions are proceeded by functional group selectively and regioselectively, using starting materials that can be easily purchased and by simplified process (that is, the numbers of steps in a process are few).

Especially, a co-cycloaddition of two alkynes with a nirile which uses transition metal complex is an attractive reaction as a straightforward method for the preparation of pyridine derivatives.

Said process is very closely related to the trimerization of alkynes to arenes, and the same catalysts such as CpCo (cod) or CpCo (CO)$_2$ are employed in these two processes.

In a case to synthesize pyridines from alkynes and nitriles, there are functional group selective and regioselective problems, similarly to the afore mentioned case of benzene derivatives preparation, which is a kind of arenes.

To overcome the problem of above mentioned producing method, various countermeasures are proposed. For example, the problem of functional group selection is proposed to be solved by the careful designing of metal complex, and the problem of regioselection is proposed to be solved by co-cycloaddition of diyne with a nitrile or by co-cycloaddition of a cyanoalkyne with an alkyne. However, said countermeasures are only partial solving, and are far from a final object. Especially, when the regioselective problem is not controlled, the synthetic technique is not a sufficient one as a synthetic technique and cannot be said as a substantial progress of synthetic techonology, even if it is completed from the view point of a functional group selection.

Therefore, the object of this invention is to develop and to provide a method for production of pyridine by which the pyridines producing reaction progresses by functional group selectively and the regioselectively, using starting material of easy purchase and by a simplified process (few step numbers of processes).

At the development of said method for production, the inventors of this invention have thought of that the method for synthesizing of pyridines regioselectively can be established using above mentioned two alkynes with one nitrile as the starting materials, based on the same theory to the technique that arenes can be regioselectively obtained from three different kinds of alkynes, which has been published recently.

The published technique for producing of said arenes is to obtain arenes by the reaction of zirconacyclopentadiene with alkyne under the presence of CuCl of chemical equivalent amount.

In the meanwhile, referring to the method for azazirconacyclopentadiene is well known, as disclosed, for example, in pages from 6802 to 6806 of J. Org. Chem. Vol 63. No.20, 1998.

The inventor of the present invention investigated the method to dissolve above-mentioned problem using the method for producing pyridines by regioselectively reacting above mentioned well-known intermediate product and second alkynes.

As the chemical reaction to produce pyridines by reacting azazircona-cyclopendadiene with alkynes, following chemical reaction scheme 1 can be supposed.

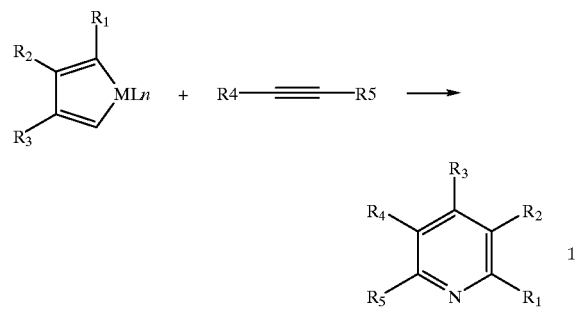

in the formula, M indicates early transition metal. L indicates cyclopentadienyl group, indenyl group, fluorenyl group, azurenyl group, hydrocarbonoxy group, amide group, acetylacetonate group, carboxyl group, phosphine ligand, amine ligand, ether ligand and ligand that these are coupled by adequate bridging group, and n indicates integer of 1 to 4. When n is bigger than 2, a combination by different ligands can be used. $R_3$, $R_4$ and $R_5$ respectively indicate a substituted or non-substituted alkyl group, alkenyl group, aromatic group, silyl group, alkoxy group or ester group of carbon number 1 to 20.

However, it become clear that azazirconacyclopendadiene alone cannot react with alkynes. Therefore, to render reaction to proceed, it is necessary to transmetalate Zr—C and Zr—N bonds of azazirconacyclopendadiene to more reactive metal-C and Metal-N bonds.

Accordingly, first of all, the inventors of this invention investigated the reaction of triethylazazirconacyclopendadiene and 3-hexene in the presence of a stoichiometric amount of CuCl.

However, the results did not meet the expectation from the method for production of arenes which controls resioselectivity in the presence of a stoichiometric amount of CuCl. On the contrary, the use of NiCl$_2$(PPh$_3$)$_2$ instead of CuCl at 50° C. results in the formation of pentaethylpyridine (2a) (in a case of R=ethyl group) in 71% yield (scheme 2).

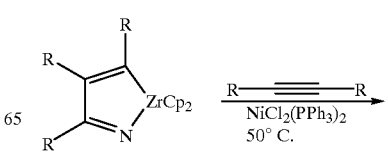

-continued

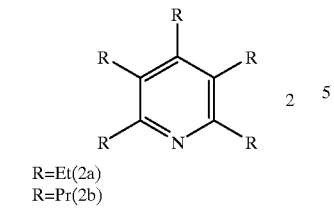

R=Et(2a)
R=Pr(2b)

The similar results are obtained for the reaction to obtain pentapropylpyridine (2b) (in a case of R=propyl group) from tripropylazazirconacyclopendadiene and 4-octyne (above mentioned scheme 2).

From these results, it becomes clear that the producing method of pyridines can be developed by the reaction mentioned above by using specific transition metal. And, by the results of further study of this reaction revealed that it can conveniently used for the preparation of homosubstituted as well as unsymmetrically substituted pyridines.

Further attention is directed to the preparation of unsymmetrically substituted pyridines by coupling of two different kinds of alkynes with nitrile. Still further, the advantage of this method is based on a sequence of selective transformations of organozirconium intermediates which is outlined in scheme 3 (mentioned below).

Therefore, the object of this invention is to provide a method to produce pyridines which is good at chemoselectivity and regioselectivity problems based on above mentioned expectation.

DISCLOSURE OF THE INVENTION

The important point of this invention is a method to produce pyridines represented by general formula (3) by the reaction of azametallacyclopentadiene represented by general formula (1) with alkynes represented by general formula (2) in organic solvent, in the presence of transition metal complex,

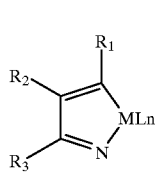

(1)

In the formula, M indicates early transition metal, desirably indicates Zr, Ti or Hf. L indicates cyclopentadienyl group, indenyl group, fluorenyl group, azurenyl group, hydrocarbonoxy group, amide group, acetylacetonate group, carboxyl group, phosphine ligand, amine ligand, ether ligand and ligand that these are coupled by adequate bridging group, and n indicates integer of 1 to 4. When n is bigger than 2, a combination by different ligands can be used. $R_1$, $R_2$ and $R_3$ respectively indicate a substituted or non-substituted alkyl group, alkenyl group, aromatic group, silyl group, alkoxy group or ester group of carbon number 1 to 20.

(2)

wherein, R4 and R5 are similar to $R_1$, $R_2$ and $R_3$, and represents respectively a substituted or non-substituted alkyl group, alkenyl group, aromatic group, silyl group, alkoxy group or ester group of carbon number 1 to 20.

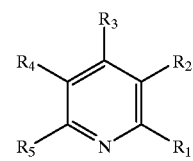

(3)

wherein, $R_1$, $R_2$, $R_3$, $R_4$ and R5 are same as above mentioned.

Desirably, a producing method of above mentioned pyridines that uses Ni (II) complex represented by general formula NiXmLn, in general formula NiXmLn, L represents a neutral ligand, n represents integer of 1 to 4. X represents an anionic ligand, m represents integer of 1 to 4. n and m can be a combination of different type ligand.

The inventors of this invention have dissolved above mentioned problem, by reacting azazirconacyclopentadiene and alkynes in the presence of a stoichiometric amount of Ni (II) complex.

THE BEST EMBODIMENT TO CARRY OUT THE INVENTION

The present invention can be readily illustrated as follows. As the concrete example, a case using azazirconacyclopentadiene is illustrated, however, this method can be, of course, applied in cases which use early transition metal besides zirconium, or in cases which uses ligands other than cyclopentadienyl.

The present invention is illustrated in further detail below. The first step is a selective generation of zirconacyclopentene 4 by the reaction of zirconacyclopentane 3 and a nitrile, and the second step is the reaction to obtain azazirconacyclopentadienes 1 by the reaction of zirconacyclopentene 4 and nitrile (scheme 3).

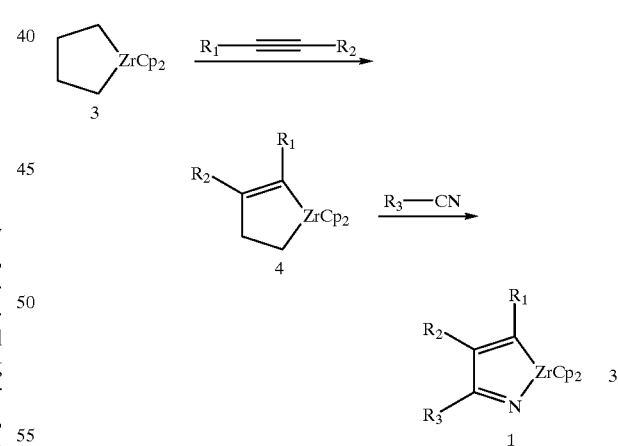

wherein, $R_1$, $R_2$ and $R_3$ are similar to mentioned above.

Therefore, azazirconacyclopentadiene having different substitution group by combination of alkynes and nitrites which have different substitution groups can be prepared.

These mentioned reactions can be referred to the methods disclosed in afore mentioned well-known documents. The especially desirable embodiment of the present invention is to obtain pyridines which has a different substitution groups by the reaction of azazirconacyclopentadiene having above mentioned substituting group and alkynes.

As the concrete examples of $R_1$ to $R_3$, alkyl group such as, methyl group, ethyl group, propyl group, isopropyl group, butyl group, isobutyl group, t-butyl group, pentyl group, neopentyl group, hexyl group, octyl group, nonyl group, decyl group, cyclopentyl group, cyclohexyl group, cyclooctyl group, alkenyl group such as, vinyl group, allyl group, 1-propenyl group, 1,2 or 3-butenyl group, 1–5 hexenyl group, cyclopentenyl group, cyclohexenyl group, cyclooctenyl group, aromatic group such as, phenyl group, naphthyl group, tolyl group, xylyl group, silyl group such as, trimethylsilyl group, triethylsilyl group, trimethoxysilyl group, triethyoxysilyl group, diphenylmethylsilyl group, dimethylphenylsilyl group, triphenylsilyl group, alkoxy group such as, methoxy group, ethoxy group, propoxy group, isopropoxy group, butoxy group, isobutoxy group, t-butoxy group, allyloxy group such as, phenoxy group, naphthoxy group, ester group such as, methylcarboxylate group, ethylcarboxylate group, propylcarboxylate group. Isopropylcarboxylate group, butylcarboxylate group, isobutylcarboxylate group, t-butylcarboxylate group, phenylcarboxylate group can be mentioned.

As the desirable group of $R_1$ to $R_3$, methyl group, ethyl group, n-butyl group, t-butyl group, hexyl group, phenyl group, trimethylsilyl group, methylcarboxylate group, ethylcarboxylate group, t-butylcarboxylate group, phenylcarboxylate group can be mentioned, more desirably, ethyl group, n-butyl group, t-butyl group, hexyl group, trimethylsilyl group and methylcarboxylate group can be mentioned.

As the concrete examples of combining group for bridging, (A) alkylene group such as methylene group, ethylene group, isopropylene group and diphenylmethylene group, (B) silylene group such as, silylene group, dimethylsilylene group, disilylene group and tetramethyldisilylene group, and (C) hydrocarbon group of carbon number 1 to 30, desirably 1 to 20 containing germanium, phosphorus, nitrogen, boron or aluminium can be mentioned. Among these, alkylene group and silylene group can be mentioned as the desirable ones.

The kind of transition metal in transition metal complex is not restricted, however, desirably transition metals of 8th to 10th families, more desirably transition metals of 10th family such as Nickel or Palladium and transition metals of 9th family such as Cobalt or Rhodium can be mentioned.

EXAMPLE

Starting materials, obtained pyridines and yields are summarized in Table 1. This approach allows to prepare pyridines with different alkyl groups 2c, 2d (entries 1 and 2), 2-arylalkylsubstituted pyridine 2e (entry 3), and pyridines with two aryl group in 2,3- and 3,4- positions 2f and 2g (entries 4 and 5).

This methodology is applicable also to azazirconaindene that after the reaction afforded substituted isoquinoline derivative 2h(entry 6).

It is noteworthy that the reaction with phenylalkylacetylenes and diphenylbutadiyne proceeds regiospecifically (entries 7 to 9) and pyridines 2i, 2j and 2k can be obtained as single regioisomers.

TABLE 1

Ni-complex mediated reaction of zirconacyclopentadienes alkynes

| | azazirconacyclo pentadiene | alkyne | reaction period | product | | yield (%)[a] |
|---|---|---|---|---|---|---|
| 1 | Et, Et, Me, ZrCp2, N | Pr—≡—Pr | 9 | Et, Et, Me, Pr, Pr, N | (2c) | 86 (66) |
| 2 | Me, Me, Ph, ZrCp2, N | Pr—≡—Pr | 6 | Me, Me, Ph, Pr, Pr, N | (2d) | 86 (52) |
| 3 | Et, Et, Ph, ZrCp2, N | Pr—≡—Pr | 6 | Et, Et, Ph, Pr, Pr, N | (2e) | 73 (57) |
| 4 | Et, Et, Me, ZrCp2, N | Ph—≡—Ph | 36 | Et, Et, Me, Ph, Ph, N | (2f) | 89 (65) |

TABLE 1-continued

Ni-complex mediated reaction of zirconacyclopentadienes alkynes

| azazirconacyclo pentadiene | alkyne | reaction period | product | | yield (%)[a] |
|---|---|---|---|---|---|
| 5 | Pr—≡—Pr | 12 | | (2g) | 77 (58) |
| 6 | Ph—≡—Ph | 72 | | (2h) | 46 (40) |
| 7 | Ph—≡—Et | 12 | | (2i) | 64 (53) |
| 8 | Ph—≡—Me | 12 | | (2j) | 52 (42) |
| 9 | Ph—≡—≡—Ph | 12 | | (2k) | 75 (44) |

[a]GC (gas chromatography) yields. Isolated yields are given in parentheses.

On the other hand, the reaction of diethylphenylazazirconacyclopentadiene with 1-phenyl-3-en-1-yne affords a mixture of two regioisomers 2l and 2m in 2.4:1 ratio (scheme 4).

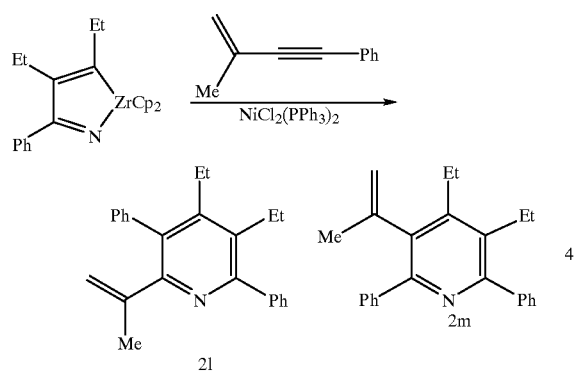

possibility to be applied in the industrial use

The present invention allows the excellent effect to prepare substituted pyridines regioselectively using different two kinds of alkynes (including alkynes used at the producing process of azametallacyclopentadiene).

What is claimed is:

1. A process for producing one or a mixture of pyridine compounds represented by general formula (3):

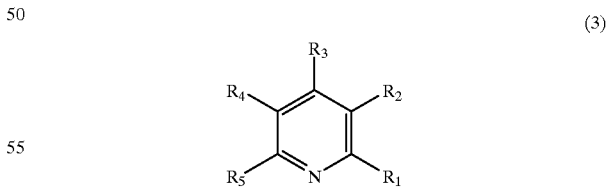

(3)

wherein $R_1$, $R_2$, and $R_3$, independently, represent substituted or non-substituted alkyl group, alkenyl group, aromatic group, silyl group, alkoxy group or ester group of carbon number 1 to 20; and, $R_4$ and $R_5$, independently, represent a substituted or non-substituted allyl group, alkenyl group, aromatic group, silyl group, alkoxy group, or ester group of carbon number 1 to 20, which comprises reacting azametallacyclopentadiene represented by general formula (1)

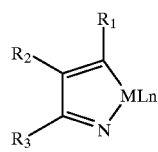
(1)

wherein
$R_1$, $R_2$, and $R_3$, are as defined above,
M represents an early transition metal;
L represents a group selected from the group consisting of cyclopentadienyl group, indenyl group, fluorenyl group, azurenyl group, hydrocarbonoxy group, amide group, acetylacetonate group, carboxyl group, phosphine ligand, amine ligand and ether ligand;
M and L may be bonded directly or via a bridging group; and,
n represents an integer of 1 to 4; and, when n is 2, 3 or 4, the groups L may be the same or different;
with at least one alkyne represented by general formula (2)

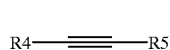
(2)

wherein $R_4$ and $R_5$ are as defined above, in organic solvent, in the presence of transition metal complex.

2. The process for producing one or a mixture of pyridine compounds according to claim 1, wherein the transition metal complex is a Ni(II) complex represented by the formula NiXmLn wherein
L represents a neutral ligand,
X represents an anionic ligand, and
m and n each, independently, represent an integer of 1 to 4, and, when m and/or n is 2 or higher, the ligands X and/or L may be the same or different.

3. The process for producing one or a mixture of pyridine compounds according to claim 1, wherein the early transition metal M is zirconium, titanium or hafnium.

4. The process for producing one or a mixture of pyridine compounds according to claim 1, wherein $R_1$, $R_2$ and $R_3$, independently, represent methyl group, ethyl group, n-butyl group, t-butyl group, hexyl group, phenyl group, trimethylsilyl group, methylcarboxylate group, ethylcarboxylate group, t-butylcarboxylate group, or phenylcarboxylate group.

5. The process for producing one or a mixture of pyridine compounds according to claim 1, wherein M and L are bonded directly.

6. The process for producing one or a mixture of pyridine compounds according to claim 1, wherein M and L are bonded via a bridging group.

7. The process for producing one or a mixture of pyridine compounds according to claim 6, wherein the bridging group is selected from the group consisting of alkylene group, silylene group and hydrocarbon group having from 1 to 20 carbon atoms containing Ge, P, N, B or Al heteroatom.

8. The process for producing one or a mixture of pyridine compounds according to claim 6, wherein the bridging group is selected from the group consisting of methylene group, ethylene group, isopropylene group, diphenylmethylene group, silylene group, dimethylsilylene group, disilylene group and tetramethyldisilylene group.

9. The process for producing one or a mixture of pyridine compounds according to claim 1, wherein in formula (1), M represents Zr and L represents cyclopentadienyl.

10. The process for producing one or a mixture of pyridine compounds according to claim 9, wherein the compound of formula (1) is selected from the group consisting of

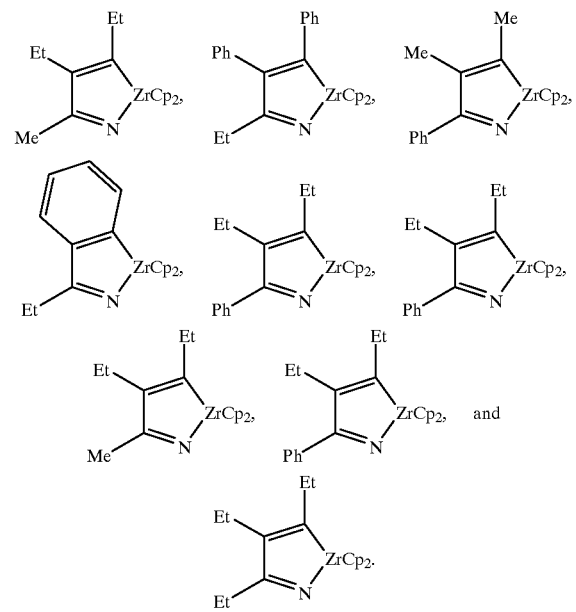

11. The process for producing one or a mixture of pyridine compounds according to claim 1, wherein the at least one alkyne of formula (2) is selected from the group consisting of

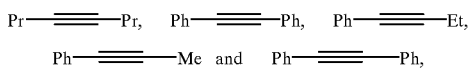

wherein Pr represents propylene group, Ph represents phenyl group, Et represents ethyl group, and Me represents methyl group.

* * * * *